United States Patent [19]

Needleman et al.

[11] Patent Number: 5,993,854

[45] Date of Patent: Nov. 30, 1999

[54] EXOTHERMIC EFFERVESCENT COMPOSITION FOR IMPROVED FRAGRANCE DISPERSION

[75] Inventors: Norman Needleman, Ivoryton, Conn.; Allen Rau, Cincinnati, Ohio

[73] Assignee: Phyzz, Inc., Cincinnati, Ohio

[21] Appl. No.: 09/007,959

[22] Filed: Jan. 16, 1998

Related U.S. Application Data

[60] Provisional application No. 60/059,198, Sep. 17, 1997.

[51] Int. Cl.⁶ .............................. A61K 9/46; A61K 7/06; A61K 7/00; A61K 9/14
[52] U.S. Cl. ................ 424/466; 424/70.1; 424/401; 424/489; 424/600; 512/1; 512/4; 512/5
[58] Field of Search ...................... 424/401, 466, 424/489, 70.1, 600; 512/1, 4, 5

[56] References Cited

U.S. PATENT DOCUMENTS 3,250,680   5/1966   Menkart et al. .
3,947,568   3/1976   Bates et al. ................ 424/47
5,238,915   8/1993   Fuwa et al. ................ 512/4
5,824,629   10/1998  Petritsch .................. 510/120

*Primary Examiner*—Shelley A. Dodson
*Assistant Examiner*—Marina Lamm
*Attorney, Agent, or Firm*—McAulay Nissen Goldberg Kiel & Hand, LLP

[57]   ABSTRACT

An aroma releasing composition has an effervescent agent, an exothermic agent and a volatile agent, the effervescent agent and exothermic agent provided in a ratio sufficient to promote release of the volatile agent, when the composition is placed in water. Such a composition has use, alone, in promoting release of fragrance agents, or in combination with a product, such as a body lotion, shampoo or liquid soap.

18 Claims, No Drawings

EXOTHERMIC EFFERVESCENT COMPOSITION FOR IMPROVED FRAGRANCE DISPERSION

This application claims benefit of Provisional application No. 60/059,198, filed Sep. 17, 1997.

TECHNICAL FIELD

This invention relates to compositions containing a volatile material such as a fragrance agent and more particularly, to compositions which promote and enhance the release of the volatile material when added to water utilizing a combination of effervescent and exothermic reactions.

BACKGROUND

Fragrances are used in many products to improve their acceptance by consumers. For example, most personal products such as moisturizers, cleansers, and even household products such as laundry detergents use fragrances to improve their consumer acceptability. There have also been many studies conducted which have speculated that aroma greatly influences human psychology and physiology, and the term "aromatherapy" has been used to describe the beneficial properties which can be achieved using fragrances. In U.S. Pat. No. 5,238,915, various aromatic compositions or perfumes are discussed in relation to aromatherapy. In the '915, the prolonged release of perfume is accomplished by a pH adjusting tablet to provide a variable release of the perfume.

Volatile materials which are inhaled are included in many medications for treating conditions such as congested sinuses and coughing. For example, menthol and camphor are recognized by the United States FDA as safe and effective for the treatment of these conditions.

Effervescent compositions are known. These compositions generally combine carbonate salts such as sodium carbonate and/or sodium bicarbonate with acidic materials such as citric, tartaric, or fumaric acid in a way that carbon dioxide is released when the product is placed in water. These products must be packaged in ways that prevent unintended contact with water so that premature reaction is avoided. Even contact with humidity in the air must be prevented during manufacture and storage as this could detrimentally effect the effervescent properties. These effervescent compositions have been used with compounds such as aspirin or acetaminophen to treat headaches and stomach upset, been added with bleach and surfactants to clean dentures such as in U.S. Pat. No. 5,384,062, and included with fragrance and moisturizers to provide bath salts.

Various compositions are known which have exothermic heats of solution. A number of these are listed in *Lange's Handbook of Chemistry*, 11th edition, in Table 9-6(P9-107). The greater the value of the heat of solution, the more heat is liberated per gram-mole of the substance. Thus, materials with higher heats of solution are able to raise the temperature of a given amount of water higher than compounds with lower heats of solution. In U.S. Pat. No. 4,818,518, a dentifrice composition is described which provides a warming sensation using an exothermic reaction.

However, there still exists in the art a need for compositions which enhance the ability to promote release of volatile materials when placed in water.

SUMMARY OF THE INVENTION

It is an object of the present invention to provide a composition capable of effervescent and exothermic reaction when mixed with water to enhance release of a volatile material, which is preferably a fragrance agent.

It is a further object of the present invention to provide a method for dispersing a volatile material by incorporating the volatile material into a solid dosage form that has both effervescent and exothermic components, with the combination of gas generation and temperature rise giving superior release and lift of the volatile material.

These and other objects of the present invention are achieved by an aromatic composition comprising an effervescent agent, an exothermic agent and a volatile agent preferably a fragrance agent, compounded into an essentially anhydrous form, the effervescent agent and exothermic agent promoting release of the volatile agent once the composition is placed in water. Tablets, powders, granules or a two-part suspensions are possible product forms.

Utilizing this combination of materials promotes and enhances release of the fragrance agent beyond that achievable by using either the effervescent or exothermic agent alone.

DETAILED DESCRIPTION OF THE INVENTION

The effervescent agent is preferably provided by combining an alkaline carbonate salt or a combination of salts such as sodium carbonate with an acid such as citric acid, malic acid, fumaric acid, succinic acid or tartaric acid. More than one acid can be used, if desired. The exact combination of acidic and alkaline materials can be varied in order to give an acidic or alkaline pH. They can also be varied to enhance the stability and physical properties of the finished product.

Among the usable alkaline carbonate salts are salts such as sodium bicarbonate, sodium carbonate, sodium sesquicarbonate, potassium bicarbonate potassium carbonate, potassium sesquicarbonate, magnesium carbonate, ammonium bicarbonate, ammonium carbonate, ammonium sesquicarbonate, and calcium carbonate. These can be used alone or in combination with each other. Of course, other effervescent agents may be used in the present invention.

Acids usable in the invention include formic acid, acetic acid, propanoic acid, butyric acid, valeric acid, oxalic acid, malonic acid, tartaric acid, succinic acid, glutaric acid, adipic acid, glycolic acid, aspartic acid, pimelic acid, fumaric acid, maleic acid, phthalic acid, isophthalic acid, terphthalic acid, glutamic acid, lactic acid, hydroxy acrylic acid, alpha hydroxy butyric acid, glyceric acid, tartronic acid, hydroxy benzoic acid, citric acid, salicylcic acid, gallic acid, mandelic acid, tropic acid, ascorbic acid, gluconic acid, cinnamic acid, benzoic acid, phenylacetic acid, nicotinic acid, kainic acid, sorbic acid, pyrrolidone carboxylic acid, trimellitic acid, benzene sulfonic acid, toluene sulfonic acid, potassium dihydrogen phosphate, sodium sulfite, sodium dihydrogen phosphate, potassium sulfite, sodium pyrosulfite, acidic sodium hexametaphosphate, acidic potassium hexametaphosphate, acidic sodium pyrophosphate, acidic potassium pyrophosphate, sulfamic acid and phosphoric acid. These can be used alone or in combination with each other. Of course, other acids may be used in the present invention.

The exothermic agent is chosen from those compounds that have positive heats of solution so that a temperature rise is achieved when the product is placed in water. Some exemplary materials are magnesium chloride, magnesium sulfate, ferric chloride, aluminum sulfate hexahydrate, and aluminum chloride. In general the material chosen should preferably have an exothermic heat of solution greater than about 10 kcal/gram-mole.

Materials with exothermic heats of solution usable in the present invention include aluminum bromide, aluminum chloride, aluminum iodide, aluminum sulfate hexahydrate, antimony pentachloride, barium hydroxide, barium iodide, barium oxide, barium oxide monohydrate, beryllium chloride, cadmium sulfate, calcium bromide, calcium chloride, calcium iodide, calcium oxide, cessium hydroxide, cessium oxide, chromium bromide hexahydrate, chromium chloride, hydrobromic acid, hydrochloric acid, hydroiodic acid, ferrous chloride, ferric chloride, litium bromide, lithium iodide, lithium oxide, magnesium bromide, magnesium chloride, magnesium sulfate, magnesium iodide, manganese chloride, manganese sulfate, neodymium chloride, nickel nitrate, phosphorous trichloride, platinum chloride, potassium oxide, potassium sulfide, rubidium oxide, sodium tetraborate, sodium phosphate, sodium selenide, sodium sulfide, strontium bromide, stannic chloride, zinc chloride, zinc bromide, zinc sulfate, and zinc iodide. Again, other exothermic agents may be used in the present invention.

The volatile material used in the composition of the invention may be ones which are able to emanate aroma or fragrance. Examples of such perfumes include natural perfumes which originate from natural plants and animals and whose aromatic ingredients are collected therefrom by physical and chemical treatments such as steam distillation, extraction and the like, chemical substances derived from resources such as coal, petroleum, natural gas, oils and fats, and perfumes prepared through chemical reactions of the natural perfumes and isolated perfumes, such as of oxidation, reduction, condensation, hydrolysis, substitution, addition and transition.

Specific examples of the perfumes include animal perfumes such as musk oil, civet, castreum, ambergris, plant perfumes such as sandalwood oil, neroli oil, bergamot oil, lemon oil, lavender oil, sage oil, rosemary oil, peppermint oil, eucalyptus oil, menthol, camphor, verbena oil, citronella oil, cauout oil, salvia oil, clove oil, chamomille oil, sandalwood oil, costus oil, labdanum oil, broom extract, carrot seed extract, jasmine extract, minmosa extract, narcissus extract, olibanum extract, rose extract and the like, and chemical substances such as acetophenonene, dimethylinadane derivatives, naphthaline derivatives, allyl caprate, α-amylcinnamic aldehyde, anethole, anisaldehyde, benzyl acetate, benzyl alcohol, benzyl propionate, borneol, cinnamyl acetate, cinnamyl alcohol, citral citronnellal, cumin aldehyde, cyclamen aldehyde, decanol, ethyl butyrate, ethyl caprate, ethyl cinnamate, ethyl vanillin, eugenol, geraniol, hexenol, α-hexylcinnamic aldehyde, hydroxycitrolnellal, indole, iso-amyl acetate, iso-amyl acetate, iso-amyl iso-valeratek iso-eugenol, linalol, linalyl acetate, p-methylacetophenone, methyl anthranilate, methyl dihydroasmonate, methyl eugenol, methyl-β-naphthol ketone, methylphenylcarbinyl acetate, musk ketol, musk xylol, 2,56-nanodinol, γ-nanolactone, phenylacetoaldehydodimethyl acetate, β-phenylethyl alcohol, 3,3,5-trimethylcyclohexanol, γ-undecalactone, undecenal, vanillin and mixtures thereof. These perfumes may be used singly or in combination of two or more, and of course, other perfumes may be used in the present invention.

The composition of the invention may further comprise arbitrary ingredients other than the above-stated essential ingredients, in amounts not impeding the effect of the aromatic composition. Such arbitrary ingredients include, for example, saccharides, surface active agents, binders, buffers, oils and fats, high molecular weight compounds and the like.

Several exemplary products were prepared by first providing an oil premix composition of 6.3% wt. eucalyptus oil, 12.7% wt. menthol, 25.3% wt. camphor, adsorbed on to 55.7% wt. maltodextrin, mixing with sodium bicarbonate in a glass mortar. Other ingredients may be used, for example, in formula 4, the oil premix was combined with a portion of sorbitol in a glass mortar. Sorbitol is used as a binder. Of course, numerous other volatile materials, including but not limited to fragrance agents and inhalants, may be used in the invention. PEG-150, a polyethylene glycol material, is used as another binder, but, various other formulating agents may be used in the inventive composition. Each mixture was then blended with all of the remaining ingredients, except for the PEG-150, in a V-blender. After 5 minutes of mixing, the PEG-150 was added to the V-blender. Mixing was continued an additional three minutes. The resulting powder mixture was discharged into a plastic bag and sealed until it was compressed into 30 gram tablets using a Colton press with 1.8366" rounded square corner, concave face, beveled edge punches. Of course, various tablet sizes can be used with the present invention, ranging from approx. 2 to approx. 100 grams per tablet.

The following charts illustrates the superiority of the invention.

| PERCENTAGE FORMULAS (by weight) | | | | | |
|---|---|---|---|---|---|
| | Formula 1 | Formula 2 | Formula 3 | Formula 4 | Formula 5 |
| Citric Acid | 25.55 | 25.55 | | 25.55 | 25.55 |
| $Na_2CO_3$ | 12.70 | 12.70 | 12.70 | | 12.70 |
| $Na_2HCO_3$ | 13.00 | 13.00 | 13.00 | | 13.00 |
| Oil Premix | 3.40 | 3.40 | 3.40 | 3.40 | 3.40 |
| $MgCl_2$ | 28.85 | | 28.85 | 28.85 | |
| $MgSO_4$ | | | | | 28.85 |
| PEG-150 | 0.50 | 0.50 | 0.50 | 0.50 | 0.50 |
| Sorbitol | 16.00 | 44.85 | 41.55 | 41.70 | 16.00 |
| TOTAL | 100.00 | 100.00 | 100.00 | 100.00 | 100.00 |

Formula 1 includes both an effervescent agent and an exotherrnic agent. Formula 2 has only an effervescent agent, Formulas 3 and 4 have an exothermic agent but no effervescent agent. Formula 5 has both.

These tablets were evaluated on the following parameters: thickness, hardness, dissolution time, temperature increase, and fragrance impact. Thickness and hardness are standard measures of tablet properties. They were evaluated using calipers and a Key hardness tester. It is generally desired to have hardness in excess of 6 kp. The dissolution time and temperature rise were measured by placing a tablet in 50 ml of 25° C. water. Fragrance impact is a subjective evaluation. Data are shown below:

| | Formula 1 | Formula 2 | Formula 3 | Formula 4 | Formula 5 |
|---|---|---|---|---|---|
| Thickness (mm) | 11.3 | 12.8 | 12.8 | 12.7 | 11.0 |
| Hardness (kp) | 12.7 | 16.1 | 11.9 | 16.7 | 9.8 |
| Dissolution time (min:sec) | 6:57 | 10:03 | 29:45 | 40:32 | 9:35 |
| Temp Rise | 29° C. | −5° C. | 19° C. | 9° C. | 10° C. |
| Fragrance Lift | Very good | Poor | Poor | Poor | Good |

Formulae 1 and 5 which include the inventive combination show that combining an effervescent agent with an exothermic agent capable of generating heat upon exposure to water gives the best dispersion and release of the volatile components. Formula 2 shows that when the heat generating material is omitted, the effervescent action actually cools the resulting solution during the reaction. Formulae 3 and 4 show that when either member of the effervescent acid/carbonate salt couple is left out, the warming effect is not sufficient to adequately disperse the volatile materials on its own.

These data clearly show that the combined effects of the effervescent reaction and exothermic reaction combine in an unexpected way to dramatically increase the lift and release of the volatile materials. Preferably, a ratio of effervescent (acid plus carbonate) to exothermic agent would be about 1 to 10, to 10 to 1, as confirmed by the following examples.

Formulations were compounded using the same method described earlier. The oil premix is the same as in previous examples: 6.3% eucalyptus oil, 12.7% menthol, 25.3% camphor adsorbed on to 55.7% maltodextrin. 30 gram tablets were prepared using a 2.25 inch diameter round die and a manually operated Carver Press. 12000 psi pressure was applied to the punches for 3 minutes to form the tablets. Since this method of forming the tablets is slightly different than that used in the previous experiments (therefore resulting in different size and thickness), tablets of formula 1 were produced again as a point of reference. The fact that the temperature rise data on these Formula 1 tablets is substantially the same as the data from the previous experiments confirms that this physical change is not significant.

|  | Formula 1 | Formula 6 | Formula 7 | Formula 8 | Formula 9 |
|---|---|---|---|---|---|
| PERCENTAGE FORMULAS (by weight) | | | | | |
| Citric Acid | 25.55 | 15.33 | 20.44 | 36.28 | 3.63 |
| $Na_2CO_3$ | 12.70 | 7.62 | 10.16 | 18.03 | 1.85 |
| $Na_2HCO_3$ | 13.00 | 7.80 | 10.40 | 18.46 | 3.40 |
| Oil Premix | 3.40 | 3.40 | 3.40 | 3.40 | 3.40 |
| $MgCl_2$ | 28.85 | 49.35 | 39.10 | 7.32 | 72.82 |
| PEG-150 | 0.50 | 0.50 | 0.50 | 0.50 | 0.50 |
| Sorbitol | 16.00 | 16.00 | 16.00 | 16.00 | 16.00 |
| TOTAL | 100.00 | 100.00 | 100.00 | 100.00 | 100.00 |
| Effervescent/Exothermic ratio | 5/3 | 3/5 | 1/1 | 10/1 | 1/10 |
| Thickness (mm) | 8.3 | 7.8 | 8.4 | 8.7 | 7.3 |
| Hardness (kp) | 17.2 | 16.7 | 20.2 | 6.0 | 19.6 |
| Dissolution time (min:sec) | 4:10 | 6:20 | 6:38 | 3:05 | 15.00 |
| Temp Rise | 27°C. | 53°C. | 42°C. | 0°C. | 44°C. |
| Fragrance lift | Very good | Excellent | Excellent | Very good | Very good |

This data confirms that the effervescent to exothermic ratios of 10/1 to 1/10 give the inventive products acceptable performance. In fact, it can be seen that manipulation of this ratio can be used to tailor the dissolution time of the product. Thus, if one wanted to extend the release of volatile material, the effervescent to exothermic ratio could be decreased without causing significant deterioration of performance.

While the composition of the invention is useful in a stand alone form, it may also be formulated with other products such as shampoo's, liquid soaps and body, skin or face lotions, where the effervescent action imparts a tingling sensation and the exothermic agent imparts a warming sensation at the same time that there is achieved optimal fragrance liberation. All of these features together would impart a unique sensory experience to the user, enhancing the effectiveness of aroma therapy. These products would be in the nature of the two part suspensions discussed earlier, where a shampoo or body lotion, for example, would be combined with the inventive composition at the time of use.

While preferred embodiments of the inventions have been shown and described, these are merely exemplary and one skilled in the art may vary these parameters without varying from the spirit and scope of the inventions.

We claim:

1. An aroma releasing composition comprising:
   an effervescent agent;
   an exothermic agent; and
   a volatile agent, the effervescent agent and exothermic agent provided in a ratio sufficient to promote release of the volatile agent, when the composition is placed in water, the agents being in an essentially anhydrous form.

2. The composition of claim 1 wherein the ratio of effervescent agent to exothermic agent is from about 1:10 to about 10:1.

3. The composition of claim 1 wherein the composition is in a granular form.

4. The composition of claim 1 wherein the composition is compounded into tablet form.

5. The composition of claim 1 wherein the composition is a suspension.

6. The composition of claim 1 wherein the effervescent agent is a combination of an alkaline carbonate salt and an acid.

7. The composition of claim 6 wherein the alkaline carbonate salt is selected from the group consisting of sodium carbonate, sodium bicarbonate, sodium sesquicarbonate, potassium bicarbonate potassium carbonate, potassium sesquicarbonate, magnesium carbonate, ammonium bicarbonate, ammonium carbonate, ammonium sesquicarbonate, calcium carbonate and combinations thereof.

8. The composition of claim 6 wherein the acid is selected from the group consisting citric acid, malic acid, fumaric acid, succinic acid, tartaric acid, formic acid, acetic acid, propanoic acid, butyric acid, valeric acid, oxalic acid, malonic acid, tartaric acid, succinic acid, glutaric acid, adipic acid, pimelic acid, fumaric acid, maleic acid, phthalic acid, isophthalic acid, terphthalic acid, glutamic acid, lactic acid, hydroxy acrylic acid, alpha hydroxy butyric acid, glyceric acid, tartronic acid, hydroxy benzoic acid, citric acid, salicylic acid, gallic acid, mandelic acid, tropic acid, ascorbic acid, gluconic acid, cinnamic acid, benzoic acid, phenylacetic acid, nicotinic acid, kainic acid, sorbic acid, pyrrolidone carboyxlic acid, trimellitic acid, benzene sulfonic acid, totuene sulfonic acid, potassium dihydrogen phosphate, sodium sulfite, sodium dihydrogen phosphate, potassium sulfite, sodium pyrosulfite, acidic sodium hexametaphosphate, acidic potassium hexametaphosphate, acidic sodium pyrophosphate, acidic potassium pyrophosphate, sulfamic aicd, phosphoric acid and combinations thereof.

9. The composition of claim 1 wherein the exothermic agent has a heat of solution greater than about 10 kcal/gram-mole.

10. The composition of claim 1 wherein the exothermic agent is selected from the group consisting of aluminum bromide, aluminum chloride, aluminum iodide, aluminum sulfate hexahydrate, antimony pentachloride, barium hydroxide, barium iodide, barium oxide, barium oxide monohydrate, beryffium chloride, cadmium sulfate, calcium bromide, calcium chloride, calcium iodide, calcium oxide, cessium hydroxide, cessium oxide, chromium bromide hexahydrate, chromium chloride, hydrobromic acid, hydrochloric acid, hydriodic acid, ferrous chloride, ferric chloride, litium bromide, lithium iodide, lithium oxide, magnesium bromide, magnesium chloride, magnesium sulfate, magnesium iodide, managanese chloride, manganese sulfate, neodymium chloride, nickel nitrate, phosphorous trichloride, platinum chloride, potassium oxide, potassium sulfide, rubidium oxide, sodium tetraborate, sodium phosphate, sodium selenide, sodium sulfide, strontium bromide, stannic chloride, zinc chloride, zinc bromide, zinc sulfate, zinc iodide and combinations thereof.

11. The composition of claim 1 wherein the volatile agent is a fragrance agent.

12. The composition of claim 1 wherein the volatile agent is selected from the group consisting of musk oil, civet, castreum, ambergris, plant perfumes, sandalwood oil, neroli oil, bergamot oil, lemon oil, lavender oil, sage oil, rosemary oil, peppermint oil, eucalyptus oil, menthol, camphor, verbena oil, citronella oil, cauout oil, salvia oil, clove oil, chamomille oil, sandalwood oil, costus oil, labdanum oil, broom extract, carrot seed extract, jasmine extract, minmosa extract, narcissus extract, olibanum extract, rose extract, acetophenonene, dimethylinadane derivatives, naphthaline derivatives, allyl caprate, α-amylcinnamic aldehyde, anethole, anisaldehyde, benzyl acetate, benzyl alcohol, benzyl propionate, borneol, cinnamyl acetate, cinnamyl alcohol, citral citronnellal, cumin aldehyde, cyclamen aldehyde, decanol, ethyl butyrate, ethyl caprate, ethyl cinnamate, ethyl vanillin, eugenol, geraniol, hexenol, α-hexylcinnamic aldehyde, hydroxycitrolnellal, indole, iso-amyl acetate, iso-amyl iso-valeratek iso-eugenol, linalol, linalyl acetate, p-methylacetophenone, methyl anthranilate, methyl dihydroasmonate, methyl eugenol, methyl-β-naphthol ketone, methylphenhlcarbinyl acetate, musk ketol, musk xylol, 2,5,6-nanodinol, γ-nanolactone, phenylacetoaldehydodimethyl acetate, β-phenylethyl alcohol, 3,3,5-trimethylcyclohexanol, γ-undecalactone, undecenal, vanillin and mixtures thereof.

13. The composition of claim 1 wherein the volatile agent is selected from the group consisting of eucalyptus oil, menthol, camphor and combinations thereof.

14. The composition of claim 1 further comprising a shampoo.

15. The composition of claim 1 futher comprising a skin lotion.

16. A method of releasing an aroma comprising: providing an essentially anhydrous, aroma releasing composition having a effervescent agent, an exothermic agent, and a volatile agent, the effervescent agent and exothermic agent provided in a ratio sufficient to promote release of the volatile agent when the composition is placed in water, and placing the composition in water.

17. The method of claim 16 further comprising mixing the aroma releasing composition with a product from the group consisting of shampoo, liquid soap and skin lotion prior to placing the composition in water.

18. The method of claim 16 wherein the ratio of effervescent agent to exothermic agent is from about 1:10 to about 10:1.

* * * * *